US012668786B2

(12) United States Patent
Guo et al.

(10) Patent No.: US 12,668,786 B2
(45) Date of Patent: Jun. 30, 2026

(54) ESTERASE AND METHODS OF USE, THEREOF

(71) Applicant: Danisco US Inc., Palo Alto, CA (US)

(72) Inventors: Feng Guo, Los Altos, CA (US); Helong Hao, Shanghai (CN); Bradley Kelemen, Menlo Park, CA (US); Amy Deming Liu, Sunnyvale, CA (US); Kefeng Ni, Shanghai (CN); Zhen Qian, Shanghai (CN); Zhongmei Tang, Shanghai (CN)

(73) Assignee: Danisco US Inc., Palo Alto, CA (US)

( * ) Notice: Subject to any disclaimer, the term of this patent is extended or adjusted under 35 U.S.C. 154(b) by 579 days.

(21) Appl. No.: 18/044,250

(22) PCT Filed: Sep. 16, 2021

(86) PCT No.: PCT/US2021/050611
§ 371 (c)(1),
(2) Date: Mar. 7, 2023

(87) PCT Pub. No.: WO2022/060942
PCT Pub. Date: Mar. 24, 2022

(65) Prior Publication Data
US 2023/0365947 A1 Nov. 16, 2023

(30) Foreign Application Priority Data
Sep. 16, 2020 (WO) ................ PCT/CN2020/115574

(51) Int. Cl.
*C08J 11/10* (2006.01)
*C12N 9/18* (2006.01)

(52) U.S. Cl.
CPC .............. *C12N 9/18* (2013.01); *C08J 11/105* (2013.01); *C08J 2301/32* (2013.01); *C08J 2367/02* (2013.01)

(58) Field of Classification Search
None
See application file for complete search history.

(56) References Cited

U.S. PATENT DOCUMENTS

2008/0274527 A1 11/2008 Soerensen et al.

OTHER PUBLICATIONS

GenPept Database Accession No. WP_081971423, Apr. 2017, 1 page (Year: 2017).*
Kawai et al., "Current State and Perspectives Related to the Polyethylene Terephthalate Hydrolases Available for Biorecycling," ACS Sustainable Chem. Eng. 8:8894-8908, May 2020 (Year: 2020).*
Yang et al., "Structural insights into the substrate specificity of two esterases from the thermophilic Rhizomucor miehei," J. Lipid Res. 56:1616-1624, 2015 (Year: 2015).*
Brackmann et al., "Enzymatic post-consumer poly(ethylene terephthalate) (PET) depolymerization using commercial enzymes," 3 Biotech 13:135, 2023 (Year: 2023).*
Singh et al., "Protein Engineering in the Post-Genomic Era," Curr. Protein Pept. Sci. 18:1-11, 2017 (Year: 2017).*
Zhang et al., "Propagated Perturbations from a Peripheral Mutation Show Interactions Supporting WW Domain Thermostability," Structure 26:1474-1485, 2018 (Year: 2018).*
Kawai, Fusako et al., Current knowledge on enzymatic PET degradation and its possible application to waste stream management and other fields, Applied Microbiology and Biotechnology, 2019, pp. 4253-4268, vol. 103.
NCBI Reference Sequence: WP_081971423.1—The ESTHER database on alpha/beta hydrolase fold proteins—An overview of recent developments, Chem Biol Interact, 2003, 383, 110671.
Ronkvist, Asa M. et al., Cutinase-Catalyzed Hydrolysis of Poly-(ethylene terephthalate), Macromolecules, 2009, pp. 5128-5138, vol. 42.
Vertommen, M.A.M.E., et al., Enzymatic surface modification of poly(ethylene terephthalate), Journal of Biotechnology, 2005, pp. 376-386, vol. 120.
International Search Report and Written Opinion—PCT/US2021/050611—Filed Sep. 16, 2021—mailed Feb. 8, 2022.

* cited by examiner

*Primary Examiner* — David Steadman

(57) ABSTRACT

The present disclosure relates to a method and a composition comprising an esterase for enzymatic surface modification of a polyester. The present disclosure also relates to a method of degradation or hydrolysis of an insoluble plant material.

5 Claims, 7 Drawing Sheets

Specification includes a Sequence Listing.

SEQUENCE LISTING

<160> NUMBER OF SEQ ID NOS: 4

<210> SEQ ID NO 1
<211> LENGTH: 265
<212> TYPE: PRT
<213> ORGANISM: Dactylosporangium aurantiacum

<400> SEQUENCE: 1

```
Met Gly Gly Gly Val Ala Ala Val Ala Thr Pro Ala Leu Ala Asp Glu
1               5                   10                  15

Ile Gly Gln Ala Pro Thr Ala Ser Asn Ile Thr Gly Asn Gly Ser Phe
            20                  25                  30

Ala Thr Thr Ser Glu Ser Ile Ser Ser Leu Val Ser Gly Phe Gly Gly
        35                  40                  45

Gly Arg Val Tyr Tyr Pro Thr Ala Thr Gly Arg Tyr Pro Val Ile Ala
    50                  55                  60

Ile Ser Pro Gly Phe Thr Ala Thr Trp Ser Ser Leu Ala Trp Ile Gly
65                  70                  75                  80

Pro Arg Leu Ser Ser Trp Gly Phe Val Val Val Gly Ile Glu Thr Asn
                85                  90                  95

Ser Ile Tyr Asp Gln Pro Gly Ser Arg Gly Asn Gln Leu Leu Ala Ala
            100                 105                 110

Leu Asn Trp Ala Val Asn Ser Ser Ser Thr Ala Val Arg Ser Arg Val
            115                 120                 125

Asp Gly Ser Arg Arg Gly Val Ala Gly His Ser Met Gly Gly Gly Gly
    130                 135                 140

Thr Leu Glu Ala Leu Ala Ala Asp Thr Ser Gly Leu Val Lys Ala Gly
145                 150                 155                 160

Val Pro Leu Ala Pro Trp Asn Thr Asp Lys Ile Trp Ser Asn Val Ser
                165                 170                 175

Glu Pro Val Leu Ile Val Gly Gly Gln Ala Asp Thr Ile Ala Pro Val
            180                 185                 190

Ala Thr His Ser Val Pro Phe Tyr Asn Thr Leu Ala Gly Pro Lys Thr
            195                 200                 205

Tyr Val Glu Leu Thr Gly Ala Ser His Phe Phe Pro Gln Thr Thr Asn
    210                 215                 220

Ala Thr Thr Ser Arg Ala Leu Val Ser Trp Phe Lys Arg Trp Leu Asn
225                 230                 235                 240

Gln Asp Ser Arg Phe Thr Pro Tyr Thr Cys Gly Phe Gly Gly Leu Ala
                245                 250                 255

Val Ser Asp Phe Arg Ser Asn Ala Cys
            260                 265
```

<210> SEQ ID NO 2
<211> LENGTH: 251
<212> TYPE: PRT
<213> ORGANISM: Dactylosporangium aurantiacum

<400> SEQUENCE: 2

```
Asp Glu Ile Gly Gln Ala Pro Thr Ala Ser Asn Ile Thr Gly Asn Gly
1               5                   10                  15

Ser Phe Ala Thr Thr Ser Glu Ser Ile Ser Ser Leu Val Ser Gly Phe
            20                  25                  30

Gly Gly Gly Arg Val Tyr Tyr Pro Thr Ala Thr Gly Arg Tyr Pro Val
        35                  40                  45

Ile Ala Ile Ser Pro Gly Phe Thr Ala Thr Trp Ser Ser Leu Ala Trp
```

-continued

```
             50              55              60
Ile Gly Pro Arg Leu Ser Ser Trp Gly Phe Val Val Val Gly Ile Glu
65                  70              75                  80

Thr Asn Ser Ile Tyr Asp Gln Pro Gly Ser Arg Gly Asn Gln Leu Leu
                85              90              95

Ala Ala Leu Asn Trp Ala Val Asn Ser Ser Ser Thr Ala Val Arg Ser
            100             105             110

Arg Val Asp Gly Ser Arg Arg Gly Val Ala Gly His Ser Met Gly Gly
        115             120             125

Gly Gly Thr Leu Glu Ala Leu Ala Ala Asp Thr Ser Gly Leu Val Lys
        130             135             140

Ala Gly Val Pro Leu Ala Pro Trp Asn Thr Asp Lys Ile Trp Ser Asn
145             150             155             160

Val Ser Glu Pro Val Leu Ile Val Gly Gly Gln Ala Asp Thr Ile Ala
                165             170             175

Pro Val Ala Thr His Ser Val Pro Phe Tyr Asn Thr Leu Ala Gly Pro
            180             185             190

Lys Thr Tyr Val Glu Leu Thr Gly Ala Ser His Phe Phe Pro Gln Thr
            195             200             205

Thr Asn Ala Thr Thr Ser Arg Ala Leu Val Ser Trp Phe Lys Arg Trp
        210             215             220

Leu Asn Gln Asp Ser Arg Phe Thr Pro Tyr Thr Cys Gly Phe Gly Gly
225             230             235             240

Leu Ala Val Ser Asp Phe Arg Ser Asn Ala Cys
            245             250
```

```
<210> SEQ ID NO 3
<211> LENGTH: 762
<212> TYPE: DNA
<213> ORGANISM: artificial sequence
<220> FEATURE:
<223> OTHER INFORMATION: synthetic construct

<400> SEQUENCE: 3
gctggaaaag atgaaatcgg acaagcacct acagcatcaa atatcacggg aaacggttct      60
tttgcaacga cgtcagaatc tatttcttca ttagttagcg gctttggcgg cggacgcgtt     120
tattatccta cggcaacggg ccgctatccg gttatcgcaa tctctccggg gttcacagca     180
acgtggtctt ctctggcatg gatcggaccg agactgtctt catggggatt tgttgttgtt     240
ggcatcgaaa caaattctat atacgatcaa ccgggctcac gcggaaatca attactggca     300
gcacttaatt gggcagttaa tagctcatct acggcagttc gctcacgcgt tgatggatct     360
agaagaggcg ttgcaggcca ttcaatgggg ggcggcggaa cacttgaagc actggcagca     420
gatacgtcag gcctggttaa agcgggtgtt cctcttgcac cgtggaatac agataaaatc     480
tggtctaatg tttcagaacc tgttctgatt gttggaggac aagcagatac gatcgcaccg     540
gttgcaacac atagcgttcc gttttataat acacttgcag acctaaaac ctatgttgaa      600 ctgacaggcg catcacattt ctttcctcaa acgacgaatg caacgacgag ccgcgcatta     660
gttagctggt ttaaaagatg gctgaatcaa gatagccgct ttacaccgta tacgtgcggc     720
tttggaggcc ttgcagttag cgattttcgc tctaatgcat gc                        762
```

```
<210> SEQ ID NO 4
<211> LENGTH: 254
<212> TYPE: PRT
<213> ORGANISM: Dactylosporangium aurantiacum
```

<400> SEQUENCE: 4

Ala Gly Lys Asp Glu Ile Gly Gln Ala Pro Thr Ala Ser Asn Ile Thr
1                5                  10                  15

Gly Asn Gly Ser Phe Ala Thr Thr Ser Glu Ser Ile Ser Ser Leu Val
            20                  25                  30

Ser Gly Phe Gly Gly Gly Arg Val Tyr Tyr Pro Thr Ala Thr Gly Arg
        35                  40                  45

Tyr Pro Val Ile Ala Ile Ser Pro Gly Phe Thr Ala Thr Trp Ser Ser
    50                  55                  60

Leu Ala Trp Ile Gly Pro Arg Leu Ser Ser Trp Gly Phe Val Val Val
65                  70                  75                  80

Gly Ile Glu Thr Asn Ser Ile Tyr Asp Gln Pro Gly Ser Arg Gly Asn
                85                  90                  95

Gln Leu Leu Ala Ala Leu Asn Trp Ala Val Asn Ser Ser Ser Thr Ala
            100                 105                 110

Val Arg Ser Arg Val Asp Gly Ser Arg Arg Gly Val Ala Gly His Ser
        115                 120                 125

Met Gly Gly Gly Gly Thr Leu Glu Ala Leu Ala Ala Asp Thr Ser Gly
    130                 135                 140

Leu Val Lys Ala Gly Val Pro Leu Ala Pro Trp Asn Thr Asp Lys Ile
145                 150                 155                 160

Trp Ser Asn Val Ser Glu Pro Val Leu Ile Val Gly Gly Gln Ala Asp
                165                 170                 175

Thr Ile Ala Pro Val Ala Thr His Ser Val Pro Phe Tyr Asn Thr Leu
            180                 185                 190

Ala Gly Pro Lys Thr Tyr Val Glu Leu Thr Gly Ala Ser His Phe Phe
        195                 200                 205

Pro Gln Thr Thr Asn Ala Thr Thr Ser Arg Ala Leu Val Ser Trp Phe
    210                 215                 220

Lys Arg Trp Leu Asn Gln Asp Ser Arg Phe Thr Pro Tyr Thr Cys Gly
225                 230                 235                 240

Phe Gly Gly Leu Ala Val Ser Asp Phe Arg Ser Asn Ala Cys
            245                 250

ESTERASE AND METHODS OF USE, THEREOF

CROSS-REFERENCE

This application is a 371 of International Application No. PCT/US2021/050611, filed Sep. 16, 2021, which claims the benefit of PCT/CN2020/115574, filed Sep. 16, 2020, and are incorporated in their entirety by reference.

FIELD

The present disclosure relates to a method and a composition comprising an esterase for enzymatic surface modification of a polyester. The present disclosure also relates to a method of degradation or hydrolysis of an insoluble plant material.

REFERENCE TO SEQUENCE LISTING SUBMITTED ELECTRONICALLY

The official copy of the sequence listing is submitted electronically via the Patent Center as an XML formatted sequence listing with a file named 20230307_NB-41838USPCT2_SeqLst created on Feb. 27, 2023 and having a size of 5659 bytes and is filed concurrently with the specification. The sequence listing contained in this XML formatted document is part of the specification and is herein incorporated by reference in its entirety.

BACKGROUND

Polyester is a category of polymers that contain the ester group in their main chain. Polyethylene terephthalate (PETE or PET) is the most commonly used thermoplastic polymer in the world and is better known in the textile industry by the trade name "polyester."

Esterases (EC 3.1.1.x) represent a diverse group of hydro-lases catalyzing the cleavage and formation of ester bonds. According to Arpigny (Arpigny, Jager, 1999 Biochem. J. 343, pp. 177-183), the esterases (EC 3.1.1) are subdivided into three different classes: the true lipases (EC 3.1.1.3), carboxyl esterases (EC 3.1.1.1) and various types of phospholipases. The hydrolytic activity on different ester bonds is important for the usefulness of the esterase in various industrial applications, such as the detergent, food, animal feed, beverage, textile, pulp and paper, organic synthesis, leather industries, and detoxification of environmental pollutants or for the treatment of polyester fabrics in the textile industry. Enzymatic surface modification of a textile is possible using esterases. The use of esterases as degrading enzymes for hydrolyzing polyethylene terephthalate (PET) is of particular interest.

PET is used extensively for insulated clothing and for furniture and pillows. PET sometimes spun together with natural fibers to produce a cloth with blended properties. Cotton-polyester blends can be strong, wrinkle- and tear-resistant, and reduce shrinking. However, due to rubbing or abrasion during normal wear and use, fine fibers that are pulled out from fabrics or knitted fabrics and which coil up to form pills or bobbles that are then only joined to the surface of the fabric or knitted fabric by a few single fibers. In artificial fibers the small bobbles of fiber adhere to the surface of the fabric. Accordingly, solutions are sought after which reduce the formation of the bobbles (de-pilling). Cellulases can be used as de-pilling agent for fabric surface, however, cellulases act exclusively on cotton fabrics. For other fabrics, such as polyester textiles, cellulases have no comparable ability to reduce pilling.

Many enzymatic treatments have been tested using various esterases, such as lipases from *Candida antarctica* (Vertommen et al. 2005), *Thermomyces lanuginosus* (Eberl et al. 2009), *Burkholderia* spp. (Lee and Chung 2009), and *Triticum aestivum* (Nechwatal et al. 2006); cutinases from fungi, *Aspergillus oryzae, Humicola insolens* (Ronqvist et al. 2009), *Penicillium citrinum* (Liebminger et al. 2007), and *Fusarium solani* (Alisch-Mark et al. 2006; O'Neill et al. 2007); and those from actinomycetes, *T. fusca* (Brueckner et al. 2008), *Thermobifida cellulosilytica* (Herrero Acero et al. 2011), *Thermobifida alba* (Ribitsch et al. 2012b), *Saccharomonospora viridis* (Kawai et al. 2017). Even a protease, papain, can improve the hydrophilicity of polyester fabrics (Kim and Song 2010).

Fermentation products, such as ethanol, are produced by degrading starch-containing material into fermentable sugars by liquefaction and saccharification and then converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining fraction is referred to as "whole stillage", which is a by-product consisting of liquids and solids remaining after recovery (e.g., by distillation) of a desired fermentation product from fermented mash (beer mash). The whole stillage is then separated using a solid-liquid separation, such as centrifugation. The solid fraction from this separation is known as wet distiller's grains (WDG), and the liquid fraction, which contains about 90-95% moisture, is thin stillage (TS) (Belyea et al. 2004).

An insoluble plant material may be a fiber, fermented mash, whole stillage, wet distiller's grains, or thin stillage, and combinations thereof. Enzymes used for degrading the insoluble plant material components include carbohydrases such as alpha-amylase, glucoamylase, cellulase and/or hemicellulase, such as xylanase, beta-glucanase, pectinase, feruloyl esterases, and acetylxylan esterase or a mixture thereof.

Thus, a need still exists for looking for an enzyme capable of modification of polyester surface, preferably reducing the pilling of textiles efficiently, especially for the synthetic fibers such as polyester, and hydrolyzing an insoluble plant material.

SUMMARY

The present disclosure relates to the methods and a composition comprising an esterase for enzymatic surface modification of a polyester. The present disclosure also relates to a method of degradation or hydrolysis of an insoluble plant material. Aspects and embodiments of the methods are described in the following, independently-numbered paragraphs.

1. In one aspect, a method for modifying an ester bond-containing polymer, comprising: contacting the ester bond-containing polymer with an effective amount of the polypeptide having polymer degradation or hydrolysis activity, wherein the polypeptide having at least about 80%, at least about 85%, at least about 90%, at least about 95%, at least about 99%, amino acid sequence identity, or identical to SEQ ID NO: 2.

2. In some embodiments of the method of paragraph 1, wherein the ester bond-containing polymer is selected from polyethylene terephthalate (PET), polytrimethylene terephthalate (PTT), polybutylen terephthalate (PBT), polyethylene isosorbide terephthalate (PEIT), polylactic acid (PLA), poly(L-lactic acid) (PLLA), poly(D-lactic acid) (PDLA), poly(D,L-lactic acid) (PDLLA), PLA stereocomplex (scPLA), polyhydroxy alkanoate (PHA), poly(3-hydroxybutyrate) (P(3HB)/ PHB), poly(3-hydroxyvalerate) (P(3HV)/PHV), poly (3-hydroxyhexanoate) (P(3HHx)), poly(3-hydroxyoc-tanoate) (P(3HO)), poly(3-hydroxydecanoate) (P (3HD)), poly(3-hydroxybutyrateco-3-hydroxyvalerate) (P(3HB-co-3HV)/PHBV), poly(3-hydroxybutyrate-co-3-hydroxyhexanoate) (P(3HB-co-3HHx)/(PHBHHx)), poly(3-hydroxybutyrate-co-5-hydroxyvalerate) (PHB5HV), poly(3-hydroxybutyrate-co-3-hydroxypro-pionate) (PHB3HP), polyhydroxybutyrate-co-hydrox-yoctonoate (PHBO), polyhydroxybutyrate-cohy-droxyoctadecanoate (PHBOd), poly(3-hydroxybu-tyrate-co-3-hydroxyvalerate-co-4-hydroxybutyrate) (P(3HB-co-3HV-co-4HB)), polybutylene succinate (PBS), polybutylen succinate adipate (PBSA), poly-butylen adipate terephthalate (PBAT), polyethylene furanoate (PEF), polycaprolactone (PCL), poly(ethyl-ene adipate) (PEA), and a mixture of one or more thereof.

3. In some embodiments of the method of paragraph 1 or 2, wherein the ester bond-containing polymer is a PET-containing polymer.

4. In some embodiments of the method of any one of paragraphs 1-3, wherein the ester bond-containing polymer is the pills on the surface of the ester bond-containing polymer.

5. In some embodiments of the method of any of the preceding paragraphs, further comprise contacting ester bond-containing polymer with one or more clean-ing agents selected from the group consisting of sur-factants, builders, bleaching agents, dye transfer inhib-iting agents, chelating agents, dispersants, polysaccharides, softening agents, suds suppressors, carriers, enzymes, enzyme stabilizing systems, polyac-ids, soil removal agents, anti-redeposition agents, hydrotropes, opacifiers, antioxidants, bactericides, dyes, perfumes, and brighteners, or a combination thereof.

6. In some embodiments of the method of paragraph 1, wherein the ester bond-containing polymer is an insoluble plant material.

7. In some embodiments of the method of paragraph 6, wherein the insoluble plant material is a hemicellulosic material.

8. In some embodiments of the method of paragraph 6, wherein the insoluble plant material is an arabinoxylan material.

9. In some embodiments of the method of any one of paragraphs 6-8, wherein the insoluble plant material is present in carbohydrate-containing feed stock, during fermentation of carbohydrate-containing feed stock, and/or in stillage obtained following the fermentation of carbohydrate-containing feed stock and distillation of ethanol produced during fermentation.

10. In some embodiments of the method of paragraph 7, wherein the hemicellulosic material is contacted prior to distillation.

11. In some embodiments of the method of paragraph 7, wherein the hemicellulosic material is contacted fol-lowing distillation.

12. In some embodiments of the method of any one of paragraphs 6-11, wherein the carbohydrate-containing feed stock is selected from corn, wheat, barley, sor-ghum, rye, or triticale, and combination thereof.

13. In some embodiments of the method of any of the preceding paragraphs, further comprise contacting the ester bond-containing polymer with one or more enzymes selected from the group consisting of pro-tease, hemicellulase, cellulase, peroxidase, esterase, xylanase, lipase, phospholipase, esterase, perhydrolase, cutinase, pectinase, pectate lyase, mannanase, kerati-nase, reductase, oxidase, phenoloxidase, lipoxygenase, ligninase, alpha-amylase, glucoamylase, pullulanase, beta-amylase, phytase, tannase, pentosanase, beta-glu-canase, arabinosidase, laccase, transferrase, and a com-bination thereof.

14. In another aspect, a recombinant construct comprising a nucleotide sequence encoding a polypeptide having polymer degradation or hydrolysis activity, wherein said coding nucleotide sequence is operably linked to at least one regulatory sequence functional in a produc-tion host and is selected from the group consisting of: the nucleotide sequence set forth in SEQ ID NO: 2 and a nucleotide sequence with at least 80% sequence identity thereto, wherein said regulatory sequence is heterologous to the coding nucleotide sequence, or said regulatory sequence and coding sequence are not arranged as found together in nature.

15. In another aspect, a recombinant host cell comprising the recombinant construct of paragraph 14.

16. In another aspect, a recombinant host cell comprising a nucleotide sequence encoding a polypeptide having polymer degradation or hydrolysis activity, wherein said coding nucleotide sequence is operably linked to at least one regulatory sequence functional in a produc-tion host and is selected from the group consisting of: the nucleotide sequence set forth in SEQ ID NO: 2 and a nucleotide sequence with at least 80% sequence identity thereto, wherein said regulatory sequence is heterologous to the coding nucleotide sequence, or said regulatory sequence and coding sequence are not arranged as found together in nature.

17. In some embodiments of the recombinant host cell of paragraph 15 or 16, which is a *Trichoderma, Aspergil-lus, Myceliopthora, E. coli, Bacillus, Streptomyces,* or Pseudomonas cell.

18. In some embodiments of the recombinant host cell of any one of paragraphs 15-17, which further expresses and secretes one or more additional enzymes selected from the group comprising protease, hemicellulase, cellulase, peroxidase, esterase, xylanase, lipase, phos-pholipase, esterase, perhydrolase, cutinase, pectinase, pectate lyase, mannanase, keratinase, reductase, oxi-dase, phenoloxidase, lipoxygenase, ligninase, alpha-amylase, glucoamylase, pullulanase, beta-amylase, phytase, tannase, pentosanase, beta-glucanase, arab-inosidase, laccase, transferrase, and a combination thereof.

19. In yet another aspect, a method of degrading a plastic product containing at least one ester bond-containing polymer comprising contacting the plastic product with an effective amount of the polypeptide having polymer degradation or hydrolysis activity, wherein the poly-peptide having at least about 80%, at least about 85%, at least about 90%, at least about 95%, at least about 99%, amino acid sequence identity, or identical to SEQ ID NO: 2.

20. In some embodiments of the method of paragraph 19, wherein the plastic product comprises at least one polymer selected from polyethylene terephthalate (PET), polytrimethylene terephthalate (PTT), polybutylen terephthalate (PBT), polyethylene isosorbide terephthalate (PEIT), polylactic acid (PLA), poly(L-lactic acid) (PLLA), poly(D-lactic acid) (PDLA), poly (D,L-lactic acid) (PDLLA), PLA stereocomplex (sc-PLA), polyhydroxy alkanoate (PHA), poly(3-hydroxybutyrate) (P(3HB)/PHB), poly(3-hydroxyvalerate) (P(3HV)/PHV), poly(3-hydroxyhexanoate) (P(3HHx)), poly(3-hydroxyoctanoate) (P(3HO)), poly(3-hydroxydecanoate) (P(3HD)), poly(3-hydroxybutyrateco-3-hydroxyvalerate) (P(3HB-co-3HV)/PHBV), poly(3-hydroxybutyrate-co-3-hydroxyhexanoate) (P(3HB-co-3HHx)/(PHBHHx)), poly(3-hydroxybutyrate-co-5-hydroxyvalerate) (PHB5HV), poly(3-hydroxybutyrate-co-3-hydroxypropionate) (PHB3HP), polyhydroxybutyrate-co-hydroxyoctonoate (PHBO), polyhydroxybutyrate-cohydroxyoctadecanoate (PHBOd), poly(3-hydroxybutyrate-co-3-hydroxyvalerate-co-4-hydroxybutyrate) (P(3HB-co-3HV-co-4HB)), polybutylene succinate (PBS), polybutylen succinate adipate (PBSA), polybutylen adipate terephthalate (PBAT), polyethylene furanoate (PEF), polycaprolactone (PCL), poly(ethylene adipate) (PEA), and a mixture of one or more thereof.

DETAILED DESCRIPTION

Figure 1A:
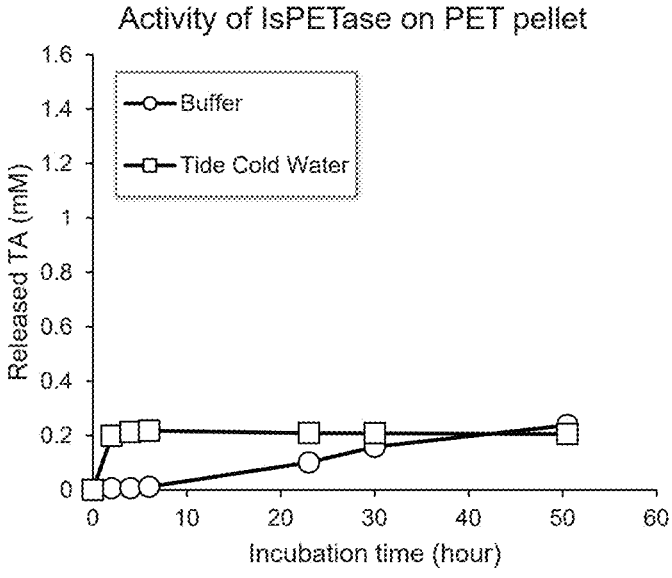
FIG. 1A shows the activity of IsPETase on PET pellets in the presence of buffer and detergent, respectively.
Figure 1B:
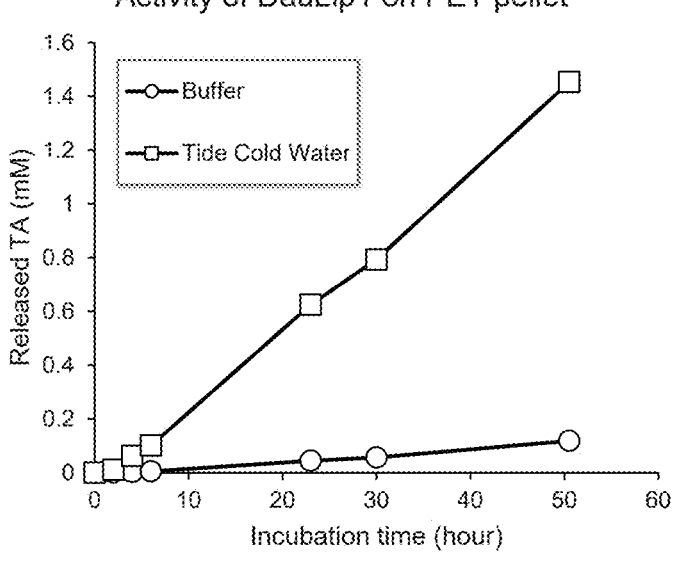
FIG. 1B shows the activity of DauLip1 on PET pellet in the presence of buffer and detergent, respectively.
Figure 1C:
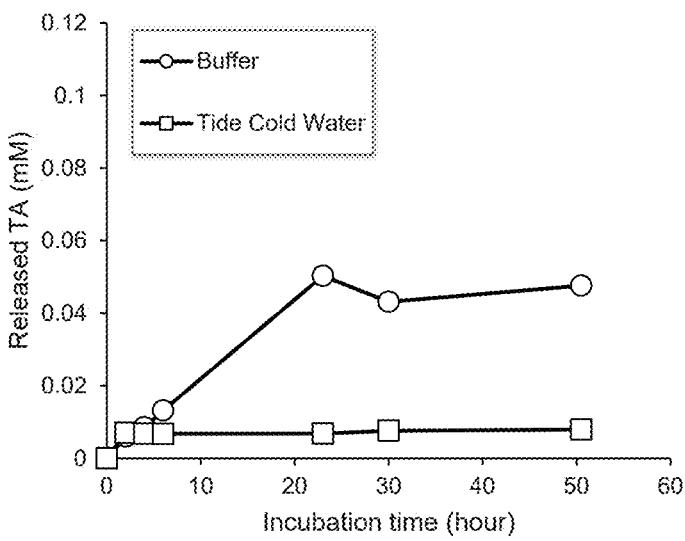
FIG. 1C shows the activity of IsPETase on PTT pellets in the presence of buffer and detergent, respectively.
Figure 1D:
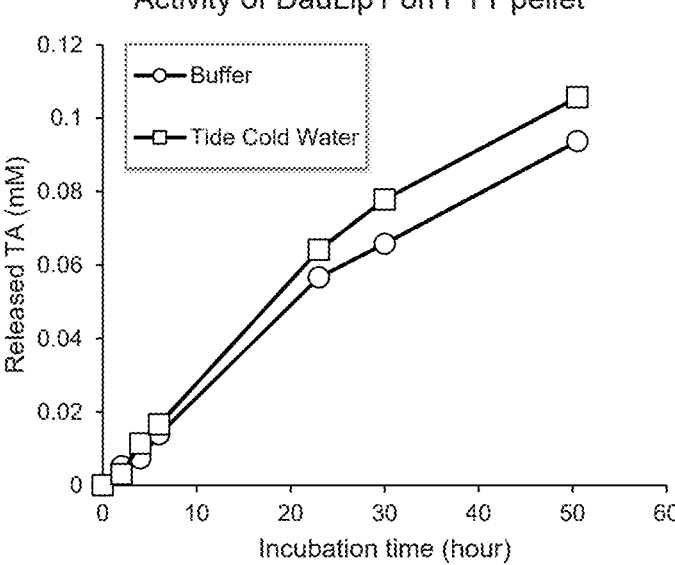
FIG. 1D shows the activity of DauLip1 on PTT pellet in the presence of buffer and detergent, respectively.

All patents, patent applications, and publications cited are incorporated herein by reference in their entirety. In this disclosure, a number of terms and abbreviations are used. The following definitions apply unless specifically stated otherwise.

The term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of". As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

Unless otherwise defined, all technical and scientific terms used have their ordinary meaning in the relevant scientific field. Singleton, et al., Dictionary of Microbiology and Molecular Biology, 2d Ed., John Wiley and Sons, New York (1994), and Hale & Markham, Harper Collins Dictionary of Biology, Harper Perennial, NY (1991) provide the ordinary meaning of many of the terms describing the invention.

As used herein, the term "polymer" refers to a chemical compound or mixture of compounds whose structure is constituted of multiple repeating units linked by covalent chemical bonds. Within the context of the disclosure, the term polymer includes natural or synthetic polymers, constituting of a single type of repeat unit (i.e., homopolymers) or of a mixture of different repeat units (i.e., block copolymers and random copolymers).

As used herein, "esterases" (EC 3.1.1.x) represent a diverse group of hydrolases catalyzing the cleavage and formation of ester bonds. According to Arpigny (Arpigny, Jager, 1999 Biochem. J. 343, pp. 177-183), the esterases (EC 3.1.1) are subdivided into three different classes: the true lipases (EC 3.1.1.3), carboxyl esterases (EC 3.1.1.1) and various types of phospholipases.

As used herein, "carboxylesterases" or "carboxyl esterases" (EC 3.1.1.1) hydrolyze ester bonds of fatty acid esters with short-chain acyl groups (Verger, 1997), compared to lipases hydrolyzing long-chain acyl groups to fatty acids and acylglycerols, corresponding to their specific hydrolytic activity.

As used herein, "lipases" (EC 3.1.1.3) represent a group of enzymes capable of degrading a triglyceride.

As used herein, "cutinases" (EC 3.1.1.74) also belong to the $\alpha/\beta$-hydrolase superfamily. They were initially discovered because they are secreted by fungi to hydrolyze the ester bonds of the plant polymer cutin. Since then, they have been shown to catalyze the hydrolysis of a variety of polymers, triacylglycerols, and low-molecular-weight soluble esters. Cutinases are also capable of catalyzing esterification and transesterification reactions.

As used herein, the term "polyester" refers to its monomer bonded by ester linkage.

As used herein, "depolymerases" or "polyester depolymerases" represent a diverse group of hydrolases having the ability to degrade polyesters. This type of the enzymes specifically acts on carboxylic ester bonds.

As used herein, the term "PET" or "polyethylene terephthalate" is commonly referred to as polyester. PET is a semiaromatic polymer synthesized from ethylene glycol and terephthalic acid.

As used herein, the term "PETase" refers to PET hydrolytic enzymes. PETases can be esterases that catalyze the hydrolysis of polyethylene terephthalate (PET) to monomeric mono-2-hydroxyethyl terephthalate (MHET). The majority of this type of enzyme comprises carboxyl esterases, lipases and cutinases able to hydrolyze PET.

As used herein, the term "whole stillage" refers a by-product consisting of liquids and solids remaining after recovery (e.g., by distillation) of a desired fermentation product from fermented mash (beer mash). Fermentation products, such as ethanol, are produced by first degrading starch-containing material into fermentable sugars by lique-faction and saccharification and then converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining fraction is referred to as "whole stillage."

The term "insoluble plant material" is an insoluble fraction derived from carbohydrate-containing feed stock. It may be present in, during fermentation of carbohydrate-containing feed stock, and/or in stillage obtained following the fermentation of carbohydrate-containing feed stock and distillation of ethanol produced during fermentation. The insoluble plant material may be a fiber, fermented mash, whole stillage, wet distiller's grains, or thin stillage, and combinations thereof.

The term "a hemicellulosic material" is a material containing hemicellulose components. Glucuronoarabinoxylans are the main hemicelluloses and are present as fiber in many food and feed products. The starch-rich seeds with economically important species such as corn have special types of highly substituted xylans in their cell walls. In corn kernel xylan, the corresponding percentage of unsubstituted backbone xylosyls is 20-30% (Huismann et al. Carbohydrate Polymers, 2000, 42:269-279). Furthermore, in corn the xylan side chains can be longer than a single arabinose or glucuronic acid substitution which is common in other xylans. About every tenth arabinose in corn kernel xylan is esterified with a ferulic acid and about every fourth xylose carries an acetylation (Agger et al. J. Agric. Food Chem, 2010, 58:6141-6148).

The term "feruloyl esterase activity" is defined herein as a 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

The term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated. The terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified."

The terms "peptides", "proteins" and "polypeptides" are used interchangeably herein and refer to a polymer of amino acids joined together by peptide bonds. A "protein" or "polypeptide" comprises a polymeric sequence of amino acid residues. The single and 3-letter code for amino acids as defined in conformity with the IUPAC-IUB Joint Commission on Biochemical Nomenclature (JCBN) is used throughout this disclosure. It is also understood that a polypeptide may be coded for by more than one nucleotide sequence due to the degeneracy of the genetic code.

The term "mature" form of a protein, polypeptide, or enzyme refers to the functional form of the protein, polypeptide, or enzyme without a signal peptide sequence or a propeptide sequence.

The term "precursor" form of a protein or peptide refers to a form of the protein having a prosequence operably linked to the amino or carbonyl terminus of the protein. The precursor may also have a "signal" sequence operably linked to the amino terminus of the prosequence.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous enzymes" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped, and a phylogenetic tree can also be built using the amino acid sequences. Sequence alignments and percent identity calculations may also be performed using the Megalign program, the AlignX program, the EMBOSS Open Software Suite (EMBL-EBI; Rice et al., *Trends in Genetics* 16, (6):276-277 (2000)) or similar programs. Multiple alignment of the sequences can also be performed using the CLUSTAL method (such as CLUSTALW) with the default parameters. Suitable parameters for CLUSTALW protein alignments include GAP Existence penalty=15, GAP extension=0.2, matrix=Gonnet (e.g., Gonnet250), protein END-GAP=−1, protein GAPDIST=4, and KTUPLE=1.

The term "nucleic acid" encompasses DNA, RNA, heteroduplexes, and synthetic molecules capable of encoding a polypeptide. Nucleic acids may be single-stranded or double-stranded, and may be chemically modified. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

The term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

A "synthetic" molecule is produced by in vitro chemical or enzymatic synthesis rather than by an organism.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "expression" refers to the process by which a polypeptide is produced based on a nucleic acid sequence. The process includes both transcription and translation.

The term "specific activity" refers to the number of moles of substrate that can be converted to product by an enzyme or enzyme preparation per unit time under specific conditions. Specific activity is generally expressed as units (U)/mg of protein.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference,"

with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

The term "about" refers to ±15% to the referenced value.

The following abbreviations/acronyms have the following meanings unless otherwise specified:

EC enzyme commission
w/v weight/volume
w/w weight/weight
v/v volume/volume
wt % weight percent
° C. degrees Centigrade
g or gm gram
μg microgram
mg milligram
kg kilogram
μL and μl microliter
mL and ml milliliter
mm millimeter
μm micrometer
mol mole
mmol millimole
M molar
mM millimolar
μM micromolar
nm nanometer
U unit
ppm parts per million
hr and h hour
ds dry solid

Esterase and Methods of Use

Esterases

The present disclosure relates to a method and a composition comprising an esterase for enzymatic surface modification of polyester. The present disclosure also relates to a method of degradation or hydrolysis of an insoluble plant material.

In a first aspect, the present disclosure provides a method for modifying an ester bond-containing polymer, comprising: contacting the ester bond-containing polymer with an effective amount of the polypeptide having polymer degradation or hydrolysis activity, wherein the polypeptide having at least about 80%, at least about 85%, at least about 90%, at least about 95%, at least about 99%, amino acid sequence identity, or identical to SEQ ID NO: 2.

The polypeptide having polymer degradation or hydrolysis activity might be an esterase. The esterase may be, for example, a lipase, a carboxyl esterase, or a cutinase. Esterases are currently being applied in multiple industries, such as the detergent, food, animal feed, beverage, textile, pulp and paper, organic synthesis, leather industries, and detoxification of environmental pollutants or for the treatment of polyester fabrics in the textile industry.

The majority of this type of enzyme comprises esterases, lipases and cutinases able to degrade or hydrolyze an ester bond-containing polymer. Carboxyl esterases, lipases and cutinases have an α/β hydrolase fold, and these enzymes typically have a catalytic triad of serine, aspartic acid and histidine residues.

In some embodiments, the enzymes having polymer degradation or hydrolysis activity of the present invention are esterases. In some embodiments, the esterases of the present invention are carboxyl esterases. In some embodiments, the esterases of the present invention are lipases. In some embodiments, the esterases of the present invention are cutinases.

In some embodiments, the esterases in the present invention are capable of catalyzing the cleavage and/or formation of ester bonds. The exemplary substrates containing ester bonds are 4-Nitrophenyl butyrate (PNB), 4-Nitrophenyl octanoate (PNO), Polyethylene terephthalate (PET).

In some embodiments, the esterases in the present invention capable of modifying an ester bond-containing polymer comprise an amino acid sequence having preferably at least 80%, at least 83%, at least 85%, at least 90%, at least 92%, at least 93%, at least 94%, at least 95%, at least 96%, at least 97%, at least 98%, and even at least 99%, amino acid sequence identity to the polypeptide of SEQ ID NO: 2.

In some embodiments, the polypeptides of the present invention are the homologous polypeptides comprising amino acid sequences differ by ten amino acids, preferably by nine amino acids, preferably by eight amino acids, preferably by seven amino acids, preferably by six amino acids, preferably by five amino acids, more preferably by four amino acids, even more preferably by three amino acids, most preferably by two amino acids, and even most preferably by one amino acid from the polypeptide of SEQ ID NO: 2.

In some embodiments, the polypeptides of the present invention are the variants of polypeptide of SEQ ID NO: 2, or a fragment thereof capable of modifying an ester bond-containing polymer.

In some embodiments, the polypeptides of the present invention may be a "chimeric" or "hybrid" polypeptide, in that it includes at least a portion of a first esterase polypeptide, and at least a portion of a second esterase polypeptide. The present esterase may further include heterologous signal sequence, an epitope to allow tracking or purification, or the like. Exemplary heterologous signal sequences are from *B. licheniformis amylase* (LAT), *B. subtilis amylase* or *protease* (AmyE or AprE), *Streptomyces CelA* and *Trichoderma reesei* CBH1.

In some embodiments, the polypeptides of the present invention have maximum activity at a temperature of about 55° C., have over 70% of maximum activity at a temperature of below 40° C. to a temperature of about 66° C., measured at a pH of 5.0, as determined by the assays described, herein. Exemplary temperature ranges for use of the enzyme are 15-70° C., 25-65° C., 45-60° C., and 50-55° C.

In some embodiments, the polypeptides of the present invention have maximum activity at a pH of about 6, have over 90% of maximum activity at a pH of about 5.5 to a pH of about 6.5, and have over 70% of maximum activity at a pH of about 4.5 to a pH of about 7.5, measured at a temperature of 50° C., as determined by the assays described, herein. Exemplary pH ranges for use of the enzyme are pH 4.0-9, 4.5-8.0, 5.0-7.5, and 5.5-7.0.

Polyester and PET

Polyesters are a category of polymers, which contain at least one ester repeating unit in their main chain polymers. In their simplest form, polyesters are produced by polycondensation reaction of a glycol (diol) with a dicarboxylic acid (diacid) or its diester. Polyesters include naturally occurring chemicals, such as in the cutin of plant cuticles, as well as synthetics through step-growth polymerization such as polybutyrate.

Polyester was commercialized in the 1950s transforming the "wash and wear" novelty into a revolution in textile product performance. As polyester garments emerged from the dryer wrinkle-free, consumers increasingly bought more garments made from polyester.

The polyester family can be divided into two major groups, aliphatic and aromatic polyesters. The aliphatic polyesters are: polyhydroxyalkanoates (PHA), which can be divided into polyhydroxybutyrate (PHB), polyhydroxyvalerate (PHV), polyhydroxyhexanoate (PHH), and their copolymers; polylactide (PLA); poly(ε-caprolactone) (PCL); polybutylenesuccinate (PBS) and its derivative poly (butylenesuccinate adipate) (PBSA). The aromatic polyesters are: modified poly(ethylene terephthalate) (PET) such as poly(butylene adipate/terephthalate) (PBAT) and poly(tetramethylene adipate-coterephthalate) (PTMAT); and aliphatic-aromatic copolyesters (AAC). Aliphatic polyesters are completely biodegradable while aromatic polyesters are almost resistant to microbial and enzymatic attack.

Poly(ethylene terephthalate) (PET), developed by DuPont in the mid-1940s, constitutes the most commonly manufactured thermoplastic because of its excellent mechanical and thermal properties. PET was first developed for use as a textile fiber (Dacron) and then applied to the fabrication of polymer films because of its transparent nature and good barrier and shatterproof properties. Subsequently, PET was processed into plastic bottles and jars by utilizing injection stretch blow molding methods. PET accounted for approximately 7% of the plastic material demand in 2015, amounting to 18.8 million tons out of the total plastic production of 269 million tons. However, PET is difficult to degrade and tend to accumulate in the environment after use, causing serious environmental disruption, termed "plastic pollution".

In some embodiments, an ester bond-containing polymer may be a polyester. In some embodiments, a polyester may be an aliphatic polyester. In some embodiments, a polyester may be an aromatic polyester. In some embodiments, an aromatic polyester maybe a polyethylene terephthalate (PET). In some embodiments, an aromatic polyester maybe a polytrimethylene terephthalate (PTT).

Esterase for Surface Modification

Any textile or film of PET may have a hydrolyzable polymer end or a loop on their surface (Kawai et al. 2017; Zimmermann and Billig 2011). Surface modification of PET fibers is needed to improve factors such as finishing fastness, dyeability, wettability, and de-pilling behavior, but degradation of the inner building block of PET is unfavourable, as it weakens the fiber strength. On the surface of PET, either fiber or film, the ends of polymer chains are expected to protrude, or a part of the polymer chain may form a loop, and these are hydrolyzed to carboxylic acid and hydroxyl residues, thus increasing surface hydrophilicity. Pilling is the formation of small, fuzzy balls on the surface of PET fabrics resulting in an unsightly worn appearance of the textile. Generally, these nodules are produced by loose fibers in the fabric or those which have been released from the tissue.

The esterases of the present invention can be used for finishing fastness, dyeability, wettability, and de-pilling. More particularly, the esterases of the present invention may be used as a detergent additive in order to reduce pilling during textile cleaning. More particularly, the esterases of the present invention have PETase activity.

Enzymes for Hydrolysis of Insoluble Plant Material

After liquefaction, saccharification and fermentation, fermented mash, known as "beer," contains up to 16% ethanol by volume and non-fermentable solids from the corn and yeast cells. The beer is pumped into continuous distillation columns, where ethanol is separated from the solids and most of the water. The water and solids remaining after distillation of ethanol is called whole stillage, comprised primarily of water, fiber, protein and fat. Typically, co-product recovery starts with whole stillage, which contains 6-16% total solids with limited shelf life. Whole stillage is usually dried for easier handling, storage, and end use. The most common practice to handle whole stillage is to transform it into a stable product which consists of a series of unit operations, first using a solid-liquid separation. The solid fraction from this separation is known as wet distiller's grains (WDG), and the liquid fraction, which contains about 90-95% of moisture, is thin stillage (TS) (Belyea et al. 2004).

In some embodiments, an ester bond-containing polymer may be an insoluble plant material presenting in carbohydrate-containing feed stock, during fermentation of carbohydrate-containing feed stock, and/or in stillage obtained following the fermentation of carbohydrate-containing feed stock and distillation of ethanol produced during fermentation.

In some embodiments the carbohydrate-containing feed stock is selected from corn, wheat, barley, sorghum, rye, or triticale, and combinations thereof.

In some embodiments, an insoluble plant material may be hemicellulosic material, preferably contacted prior to distillation, or preferably contacted following distillation.

In some embodiments, insoluble plant material may be fiber, fermented mash, whole stillage, wet distiller's grains, or thin stillage, and combinations thereof.

Enzymes used for degrading an insoluble plant material include carbohydrases such as alpha-amylase, glucoamylase, cellulase and/or hemicellulase, such as xylanase, beta-glucanase, pectinase, feruloyl esterases, and acetylxylan esterase or a mixture thereof.

Production of Esterases

The present esterases can be produced in host cells, for example, by secretion or intracellular expression. A cultured cell material (e.g., a whole-cell broth) comprising an esterase can be obtained following secretion of the esterase into the cell medium. Optionally, the esterase can be isolated from the host cells, or even isolated from the cell broth, depending on the desired purity of the final esterase. A gene encoding an esterase can be cloned and expressed according to methods well known in the art.

In some embodiments, the host cells are prokaryotic cells. In some embodiments, the host cells are eukaryotic cells.

In some embodiments, the prokaryotic cells are selected from the group comprising: *Bacillus subtilis, B. licheniformis*, or *Streptomyces*. In some embodiments, the eukaryotic cells are selected from the group comprising: *Trichoderma, Penicillium, Aspergillus, Humicola, Chrysosporium, Fusarium, Neurospora*, and *Emericella*. In other embodiments, the eukaryotic cells are selected from the group comprising: *Issatchenkia, Pichia, Clavispora, Candida, Hansenula, Kluyveromyces, Saccharomyces, Schizosaccharomyces, Kloeckera, Schwanniomyces, Blakeslea, Cryptococcus, Cunninghamella, Lipomyces, Mortierella, Mucor, Phycomyces, Pythium, Rhodosporidum, Rhodotorula, Trichosporon and Yarrowia*. Particularly useful host cells include *Aspergillus niger, Aspergillus oryzae* or *Trichoderma reesei*.

It is advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

A DNA construct comprising a nucleic acid encoding esterase can be constructed to be expressed in a host cell. Because of the well-known degeneracy in the genetic code, different polynucleotides that encode an identical amino acid sequence can be designed and made with routine skill. It is also well-known in the art to optimize codon use for a particular host cell. Nucleic acids encoding esterase can be incorporated into a vector. Vectors can be transferred to a host cell using well-known transformation techniques, such as those disclosed below. A representative vector is p2JM, a derivative of p2JM103BBI (Vogtentanz, Protein Expr Purf 55:40-52, 2007), for *B. subtilis* expression. p2JM contains an aprE promoter, an aprE signal sequence used to direct target protein secretion in *B. subtilis*. Another representative vector is pTrex3gM (see US 20130323798), that can be inserted into genome of host. pTrex3gM can be modified with routine skill to comprise and express a nucleic acid encoding an esterase variant.

A nucleic acid encoding an esterase can be operably linked to a suitable promoter, which allows transcription in the host cell. The promoter may be any DNA sequence that shows transcriptional activity in the host cell of choice and may be derived from genes encoding proteins either homologous or heterologous to the host cell. Exemplary promoters for directing the transcription of the DNA sequence encoding an esterase, especially in a bacterial host, are the promoter of the lac operon of *E. coli*, the *Streptomyces coelicolor* agarase gene dagA or celA promoters, the promoters of the *Bacillus licheniformis* amylase gene (amyL), the promoters of the *Bacillus stearothermophilus* maltogenic amylase gene (amyM), the promoters of the *Bacillus amyloliquefaciens* amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase.

An expression vector may also comprise a suitable transcription terminator and, in eukaryotes, polyadenylation sequences operably linked to the DNA sequence encoding an esterase. Termination and polyadenylation sequences may suitably be derived from the same sources as the promoter.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra.

A method of producing an esterase may comprise cultivating a host cell under conditions conducive to the production of the enzyme and recovering the enzyme from the cells and/or culture medium.

An enzyme secreted from the host cells can be used in a whole broth preparation. In the present methods, the preparation of a spent whole fermentation broth of a recombinant microorganism can be achieved using any cultivation method known in the art resulting in the expression of an esterase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the esterase to be expressed or isolated.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Composition Comprising the Esterase

In a second aspect, the present disclosure provides a composition for modifying an ester bond-containing polymer, comprising a polypeptide having polymer degradation or hydrolysis activity, wherein the polypeptide having at least about 80%, at least about 85%, at least about 90%, at least about 95%, at least about 99%, amino acid sequence identity, or identical to SEQ ID NO: 2.

In some embodiments, the detergent compositions further comprise one or more additional cleaning components. The choice of additional components is within the skill of the artisan and includes conventional ingredients, including the exemplary non-limiting components set forth below.

In some embodiments, the cleaning or detergent compositions of the present disclosure further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference).

The detergent or cleaning compositions of the present invention are advantageously employed for example, in laundry applications, hard surface cleaning, dishwashing applications, as well as personal care or cosmetic applications such as dentures, toothpastes, cosmetics, lotions, shampoos, conditioners, creams, wipes, pre-moistened wipes, balms, pastes, or ointments. In addition, due to the unique advantages of increased effectiveness in lower temperature solutions, the enzymes of the present invention are ideally suited for laundry applications. Furthermore, the enzymes of the present invention find use in granular and liquid compositions.

Enzyme component weights are based on total active protein. All percentages and ratios are calculated by weight unless otherwise indicated. All percentages and ratios are calculated based on the total composition unless otherwise indicated. In laundry detergent compositions, the enzyme levels are expressed in ppm, which equals mg active protein/kg detergent composition.

In some embodiments, the laundry detergent compositions described herein further comprise a surfactant. In some embodiments, the surfactant is selected from a non-ionic, ampholytic, semi-polar, anionic, cationic, zwitterionic, and combinations and mixtures thereof. In yet a further embodiment, the surfactant is selected from an anionic surfactant, a cationic surfactant, a zwitterionic surfactant, and combinations thereof. In some embodiments, the laundry detergent compositions described herein comprise from about 0.1% to about 60%, about 1% to about 50%, or about 5% to about 40% surfactant by weight of the composition.

Exemplary surfactants include, but are not limited to sodium dodecylbenzene sulfonate, C12-14 pareth-7, C12-15 pareth-7, sodium C12-15 pareth sulfate, C14-15 pareth-4, sodium laureth sulfate (e.g., Steol CS-370), sodium hydrogenated cocoate, C12 ethoxylates (Alfonic 1012-6, Hetoxol LA7, Hetoxol LA4), sodium alkyl benzene sulfonates (e.g., Nacconol 90G), and combinations and mixtures thereof. Anionic surfactants include but are not limited to linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0-40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, polyhydroxy alkyl fatty acid amide (e.g., as described in WO 92/06154), and combinations and mixtures thereof.

Nonionic surfactants that may be used with the detergent compositions described herein include but are not limited to polyoxyethylene esters of fatty acids, polyoxyethylene sorbitan esters (e.g., TWEENs), polyoxyethylene alcohols, polyoxyethylene isoalcohols, polyoxyethylene ethers (e.g., TRITONs and BRIJ), polyoxyethylene esters, polyoxyethylene-p-tert-octylphenols or octylphenyl-ethylene oxide condensates (e.g., NONIDET P40), ethylene oxide condensates with fatty alcohols (e.g., LUBROL), polyoxyethylene nonylphenols, polyalkylene glycols (SYNPERONIC F108), sugar-based surfactants (e.g., glycopyranosides, thioglycopyranosides), and combinations and mixtures thereof.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a H2O2 source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

The detergent additive as well as the detergent composition may comprise one or more additional enzymes, such as acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, feruloyl esterase, galactanases, glucoamylases, hemicellulases, hexosaminidases, hyaluronidases, keratinases, laccases, lactases, ligninases, lipases, lipoxygenases, mannanases, metalloproteases, nucleases (e.g. deoxyribonucleases and ribonucleases), oxidases, oxidoreductases, pectate lyases, pectin acetyl esterases, pectinases, pentosanases, perhydrolases, peroxidases, phenoloxidases, phosphatases, phospholipases, phytases, polygalacturonases, polyesterases, proteases, pullulanases, reductases, rhamnogalacturonases, beta-glucanases, tannases, transglutaminases, xylan acetylesterases, xylanases, xyloglucanases, xylosidases, and any combination or mixture thereof.

In general, the properties of the one or more enzymes should be compatible with the selected detergent, (i.e., pH optimum, compatibility with other enzymatic and non-enzymatic ingredients, etc.), and should be present in effective amounts.

A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

The detergent composition may be in any convenient form, for example, a bar, a homogenous tablet, a tablet having two or more layers, a pouch having one or more compartments, a regular or compact powder, a granule, a paste, a gel, or a regular, compact or concentrated liquid.

EXAMPLES

Aspects of the present methods and compositions may be further understood in light of the following examples, which should not be construed as limiting. Modifications to materials and methods will be apparent to those skilled in the art.

Example 1

Expression of DauLip1 Esterase

The amino acid sequence of the *Dactylosporangium aurantiacum* esterase (DauLip1) was found in the NCBI database (Accession No. WP_081971423.1). At the N-terminus, the protein has a signal peptide with a length of 14 amino acids as predicted by SignalP-NN (Emanuelsson et al., Nature Protocols, 2:953-971, 2007). The presence of a signal sequence suggests that DauLip1 is a secreted enzyme.

DauLip1 was expressed in *Bacillus subtilis* using the expression vector p2JM103BBI (Vogtentanz, Protein Expr Purif, 55:40-52, 2007). This plasmid contains an aprE promoter, an aprE signal sequence used to direct target protein secretion in *B. subtilis*, an oligonucleotide named AGK-proAprE that encodes peptide Ala-Gly-Lys to facilitate the secretion of the target protein (See United States Patent Application US20170159036A1), and the synthetic nucleotide sequence encoding the mature region of target gene. Competent *B. subtilis* cells were transformed and plated on Luria Agar plates supplemented with 5 ppm chloramphenicol. Colonies were picked and subjected to fermentation in a 250 ml shake flask with MBD medium (a MOPS based defined medium, supplemented with additional 5 mM CaCl$_2$). Supernatants from these cultures were used to confirm the protein expression by SDS-PAGE analysis and assay for enzyme activity.

The amino acid sequence of the full-length form of DauLip1 esterase is set forth as SEQ ID NO: 1. The predicted native signal peptide is shown in italics.

```
mgggvaavatpaladeigqaptasnitgngsfattsesisslvsgfgggr vyyptatgrypviaispgftatwsslawigprlsswgfvvvgietnsiyd qpgsrgnqllaalnwavnssstavrsrvdgsrrgvaghsmggggtleala adtsglvkagvplapwntdkiwsnvsepvlivggqadtiapvathsvpfy ntlagpktyveltgashffpqttnattsralvswfkrwlnqdsrftpytc gfgglavsdfrsnac
```

The protein sequence of predicted mature form of the DauLip1 esterase is set forth as SEQ ID NO: 2.

```
DEIGQAPTASNITGNGSFATTSESISSLVSGFGGGRVYYPTATGRYPVIA

ISPGFTATWSSLAWIGPRLSSWGFVVVGIETNSIYDQPGSRGNQLLAALN

WAVNSSSTAVRSRVDGSRRGVAGHSMGGGGTLEALAADTSGLVKAGVPLA

PWNTDKIWSNVSEPVLIVGGQADTIAPVATHSVPFYNTLAGPKTYVELTG

ASHFFPQTTNATTSRALVSWFKRWLNQDSRFTPYTCGFGGLAVSDFRSNA

C
```

The synthetic nucleotide sequence of DauLip1 esterase gene in the expression plasmid is set forth as SEQ ID NO: 3. The AGK-proAprE oligonucleotide is shown in bold:

```
gctggaaaaGATGAAATCGGACAAGCACCTACAGCATCAAATATCACGGG

AAACGGTTCTTTTGCAACGACGTCAGAATCTATTTCTTCATTAGTTAGCG

GCTTTGGCGGCGGACGCGTTTATTATCCTACGGCAACGGGCCGCTATCCG

GTTATCGCAATCTCTCCGGGGTTCACAGCAACGTGGTCTTCTCTGGCATG

GATCGGACCGAGACTGTCTTCATGGGGATTTGTTGTTGTTGGCATCGAAA

CAAATTCTATATACGATCAACCGGGCTCACGCGGAAATCAATTACTGGCA

GCACTTAATTGGGCAGTTAATAGCTCATCTACGGCAGTTCGCTCACGCGT
```

-continued

```
TGATGGATCTAGAAGAGGCGTTGCAGGCCATTCAATGGGGGCGGCGGAA

CACTTGAAGCACTGGCAGCAGATACGTCAGGCCTGGTTAAAGCGGGTGTT

CCTCTTGCACCGTGGAATACAGATAAAATCTGGTCTAATGTTTCAGAACC

TGTTCTGATTGTTGGAGGACAAGCAGATACGATCGCACCGGTTGCAACAC

ATAGCGTTCCGTTTTATAATACACTTGCAGGACCTAAAACCTATGTTGAA

CTGACAGGCGCATCACATTTCTTTCCTCAAACGACGAATGCAACGACGAG

CCGCGCATTAGTTAGCTGGTTTAAAAGATGGCTGAATCAAGATAGCCGCT

TTACACCGTATACGTGCGGCTTTGGAGGCCTTGCAGTTAGCGATTTTCGC

TCTAATGCATGC
```

The amino acid sequence of the mature form of the DauLip1 esterase confirmed by mass spectroscopy analysis is set forth below as SEQ ID NO: 4:

```
AGKDEIGQAPTASNITGNGSFATTSESISSLVSGFGGGRVYYPTATGRYP

VIAISPGFTATWSSLAWIGPRLSSWGFVVVGIETNSIYDQPGSRGNQLLA

ALNWAVNSSSTAVRSRVDGSRRGVAGHSMGGGGTLEALAADTSGLVKAGV

PLAPWNTDKIWSNVSEPVLIVGGQADTIAPVATHSVPFYNTLAGPKTYVE

LTGASHFFPQTTNATTSRALVSWFKRWLNQDSRFTPYTCGFGGLAVSDFR

SNAC
```

The PETase from the bacterium *Ideonella sakaiensis* (Yoshida et al., Science, 351(6278):1196-1199, 2016) was cloned and expressed in *Bacillus subtilis* as described in IP.com with publication Number: IPCOM000262553D. The accession number for the protein sequence of IsPETase in the NCBI database is WP_054022242.1.

The amino acid sequence of the full-length form of IsPETase is set forth as SEQ ID NO: 5. The predicted native signal peptide is shown in italics.

```
MNFPRASRLMQAAVLGGLMAVSAAATAQTNPYARGPNPTAASLEASAGPF

TVRSFTVSRPSGYGAGTVYYPTNAGGTVGAIAIVPGYTARQSSIKWWGPR

LASHGFVVITIDTNSTLDQPSSRSSQQMAALRQVASLNGTSSSPIYGKVD

TARMGVMGWSMGGGGSLISAANNPSLKAAAPQAPWDSSTNFSSVTVPTLI

FACENDSIAPVNSSALPIYDSMSRNAKQFLEINGGSHSCANSGNSNQALI

GKKGVAWMKRFMDNDTRYSTFACENPNSTRVSDFRTANCS
```

The crude broth from shake flask was concentrated and ammonium sulfate was added to it to final concentration of 1 M. The solution was stirred for 1 h, and kept for 30 min at 4° C., then centrifuged at 8,000 g for 30 min. The pellet was re-suspended in 20 mM sodium phosphate—pH 6.0 (buffer A). The resulting solution was applied to a HiPrep™ SP FF 16/10 column pre-equilibrated with Buffer A. The target protein was eluted from the column with a linear salt gradient from 0 to 0.5 M NaCl in buffer A. The fractions containing target protein were then pooled and concentrated via the 10K Amicon Ultra devices and stored in 40% glycerol at −20° C. until usage.

Example 2

Biochemical Characterization of DauLip1 Esterase

The specific activity of DauLip1 esterase was assayed using 4-nitropheyl octanoate (pNO) as substrate. Substrate solution (1 mM) was prepared by adding 1 mL of pNO stock solution (20 mM in DMSO) to 19 mL of buffer (50 mM, pH 8.0 HEPES or pH 5.0 sodium acetate) containing 2 mM of $CaCl_2$ and 0.5% (w/w) of Triton X-100. Serial dilution of enzyme sample and 4-Nitrophenol standard were prepared in MilliQ water. 10 uL of enzyme sample was transferred into a new microtiter plate (Corning 3641) containing 90 µL of substrate solution preincubated at 40° C. for 5 min at 650 rpm. The reaction was carried out at 40° C. for 10 min with shaking (650 rpm) in an iEMS shaker (Thermofisher). At the end of incubation, 50 µL of HEPES buffer (1 M, pH 8.0) was quickly transferred to the assay plate. The plate was mixed well and measured at 405 nm on Microplate reader (Molecular devices, SpectraMax plus 384).

Resulting absorbance values were plotted against enzyme concentration and linear regression was used to determine the slope of the linear region of the plot. One enzyme unit is defined as the amount of enzyme required to generate 1 µmole of nitrophenol per minute under the conditions of the assay. The specific activity of enzyme was calculated based on the 4-nitrophenol standard curve using Equation 1:

$$\text{Specific activity (Unit/mg)} = \text{Slope (enzyme)/Slope (standard)} * 100,$$

$$\text{Where 1 Unit} = 1 \, \mu\text{mole 4-nitrophenol/min.}$$

The pH and temperature profile of DauLip1 esterase were determined using pNO as substrate. For temperature profile, the reaction mixtures were incubated in Thermo Cycler (T100, Bio-Rad) with temperature gradient from 40° C. to 90° C. for 10 min. For pH profile, substrate solutions with pH range from 3.0 to 7.0 were prepared by diluting the pNO in a glycine/sodium acetate/HEPES buffer system to final 1 mM. The reaction was carried out at 40° C. for 10 min. The amount of free 4-nitrophenol was quantified by measuring the absorbance at 405 nm.

The resulting values were converted to percentages of relative activity by defining the maximal activity at the optimal pH/temperature as 100%. The pH/temperature range is defined by the range of pH/temperature in which enzyme retained at least 70% of its maximal activity.

The basic biochemical properties of DauLip1 esterase are summarized in Table 1.

TABLE 1

| Biochemical properties of DauLip1 esterase | |
| --- | --- |
| Biochemical property | Result |
| Specific activity at pH 5.0 (U/mg) | 211.69 |
| Specific activity at pH 8.0 (U/mg) | 184.97 |
| Optimum pH | 6 |
| pH range | 4.8-7.3 |
| Optimum Temperature (° C.) | 55 |
| Temperature range (° C.) | <40-65.5 |

Example 3

Activity of DauLip1 Esterase on Amorphous PET Powder

The activity of DauLip1 esterase on PET was determined using amorphous PET powder (Scientific Polymer Products, Cat#138) as substrate. The enzyme performance was evaluated by measuring the released terephthalic acid (TA) monomer or its hydroxyethyl esters after enzymatic reaction by reading the absorbance at 240 nm.

Substrate solution was prepared by weighing 1 g of amorphous PET powder in a beaker, adding 100 mL of HEPES buffer (pH 8.0, 50 mM with 16 gpg water hardness Ca:Mg=3:1) to suspense the substrate. Heat-inactivated detergent was added. The substrate solution was kept mixing with a magnetic stirrer, 135 µL of the substrate solution was transferred to a microtiter plate (Nunc, 267245) by multichannel pipette with wide-bore tips. Serial dilution of enzyme sample and terephthalic acid standard were prepared in MilliQ water. 15 µL of enzyme sample was added to the assay plate to initiate the reaction. The reaction was carried out at 40° C. for 20 hours with shaking (300 rpm) in incubation shaker (Infors HT, Multitron). After incubation, the reaction supernatant was collected by filtration using a filter plate (Corning 3505). 100 µL of the supernatant was transferred into a new UV-transparent plate (Corning 3635) and measured at 240 nm on Microplate reader (Molecular devices, SpectraMax plus 384).

Liquid detergents, Persil Pro Clean (Unilever) and Tide Cold Water (P&G) were purchased from US supermarkets. Liquid detergents, Persil Color Gel (Unilever) and Persil Non-Bio (Unilever) were purchased from European supermarkets. Test HDL 1 detergent was custom-made in house and the composition is set forth in Tables 2.

TABLE 2

Composition of Custom-made Test HDL 1 Detergent Formula

| Component | Ingredient | Trade name | Wt. % |
|---|---|---|---|
| Solvent | Water (total) | — | 64.89 |
| Surfactant | C12-C15 Pareth-7 (Sodium) | Empilan KCL 7 | 3 |
| | Dodecylbenzenesulfonate | NANSA SSA F | 7.5 |
| | K-Cocoate | NANSA PC 38F | 3 |
| | Sodium Laureth Sulfate | Empicol ESB3/M6 | 9 |
| Builder | Sodium Citrate | Sodium Citrate Tribasic Dihydrate | 3 |
| Liquid properties/ stability | Sorbitol | D-Sorbitol | 0.8 |
| | Propylene glycol | 1,2-Propanediol | 2.5 |
| | Glycerin | Glycerol | 0.8 |
| | Triethanolamine | Triethanolamine | 0.5 |
| | Methylisothiazolinone | 2-Methyl-4-isothiazolin-3-one | 0.01 |
| | Ethanol | — | 1 |
| Neutralizer | NaOH (4M) | — | 5.27 |

Resulting absorbance values were plotted against enzyme concentration and linear regression was used to determine the slope of the linear region of the plot. One enzyme unit is defined as the amount of enzyme required to generate 1 µmole of terephthalic acid per hour under the conditions of the assay. The specific activity of enzyme was calculated based on the terephthalic acid standard curve using Equation 2:

$$\text{Specific activity (Unit/mg)} = \text{Slope (enzyme)}/\text{Slope (standard)} * 1000/20,$$

Where 1 Unit = 1 µmole terephthalic acid/hour.

Using the method mentioned above, specific activity of DauLip1 esterase on amorphous PET powder in the presence of different detergents were determined and the results are summarized in Table 3.

TABLE 3

Activity of DauLip1 on amorphous PET powder

| Detergent | Detergent dosage | DauLip1 | IsPETase |
|---|---|---|---|
| Persil Non-Bio | 2.7 g/L | 5.74 | 3.82 |
| Persil Color Gel | 6.6 g/L | 8.11 | 6.41 |
| Tide Cold Water | 0.89 g/L | 10.34 | 5.00 |
| Persil Pro Clean | 3 g/L | 10.05 | 13.24 |
| Test HDL 1 | 3 g/L | 6.98 | 1.67 |

Example 4

Activity of DauLip1 on Polymer Pellets

The activity of DauLip1 on polymer pellets were determined using amorphous PET pellets (Scientific Polymer Products, Cat#138) and PTT pellets (DuPont, Sorona® FG3301 NC010) as substrates.

1 piece/well of polymer pellet was added to a 96-well deep well plate (Axygen), 1 mL of HEPES buffer (50 mM, 16 pgp water hardness, Ca:Mg=3:1, pH 8.0) was then added. The activity of enzyme in the presence of detergents were also measured using the same buffer with either 0.89 g/L of heat-inactivated Tide Cold Water detergent or 3 g/L of Test HDL 1 detergent. The reaction was carried out at 40° C. with shaking (300 rpm) in incubation shaker (Infors HT, Multitron). At each time-point, 60 µL of the reaction mixture was taken and filtered by filter plate. 40 µL of supernatant was transferred into a 384-well UV transparent plate (Greiner) and measured at 240 nm on Microplate reader (Molecular devices, SpectraMax plus 384). The release monomers (Released TA) amount was calculated based on a terephthalic acid standard curve. The results are illustrated in FIGS. 1A-D. Both DauLip1 and IsPETase showed positive hydrolysis activity on PET pellet in the buffer. However, the activity of DauLip1 on PET pellet was significantly improved in the presence of detergents, especially Tide Cold Water. For PTT pellet, both enzymes showed positive activity in the buffer. But the activity of IsPETase on PTT pellet decreased in the presence of detergents, while the activity of DauLip1 was slightly improved by Tide Cold Water.

Example 5

Modification of Hemicellulose Material by DauLip1 Enzyme

The performance of DauLip1 on the modification of arabinoxylan was determined using the washed whole stillage solid (from corn) as the substrate. The water-extractable arabinoxylan polymers released by enzyme treatment was hydrolyzed using sulfuric acid at high temperature. The amount of the sugar monomers was then quantified by HPLC.

Preparation of insoluble fiber. The insoluble solids of corn grain feedstock samples after distillation, i.e. whole stillage slurry, from a corn grain ethanol facility were collected by centrifugation. The liquid fraction was decanted. The solids were suspended in deionized water and collected by centrifugation again. The process of suspending solids with water and centrifugation was repeated three more times for a total of four water washes. The water-washed solids were suspended with ethanol (200 proof) and centrifuged to remove the liquid phase by decanting. The process of suspending solids with ethanol and centrifugation was repeated two more times for a total of three ethanol washes. The solids were dried at room temperature to remove residual ethanol. The fibrous material was combined with an equal mass of dry ice and cryo-size reduced to 0.5 millimeter in a centrifugal mill (Retsch Ultra Centrifugal Mill ZM 200).

Micro-scale enzyme activity. Insoluble fiber solids were suspended at 3% wt/wt in 20 mM sodium acetate pH 5.0. The insoluble solids were kept in suspension with constant magnetic stirring. The slurry was distributed to wells of 96-well reaction plates using wide-bore pipette tips.

Figure 2:
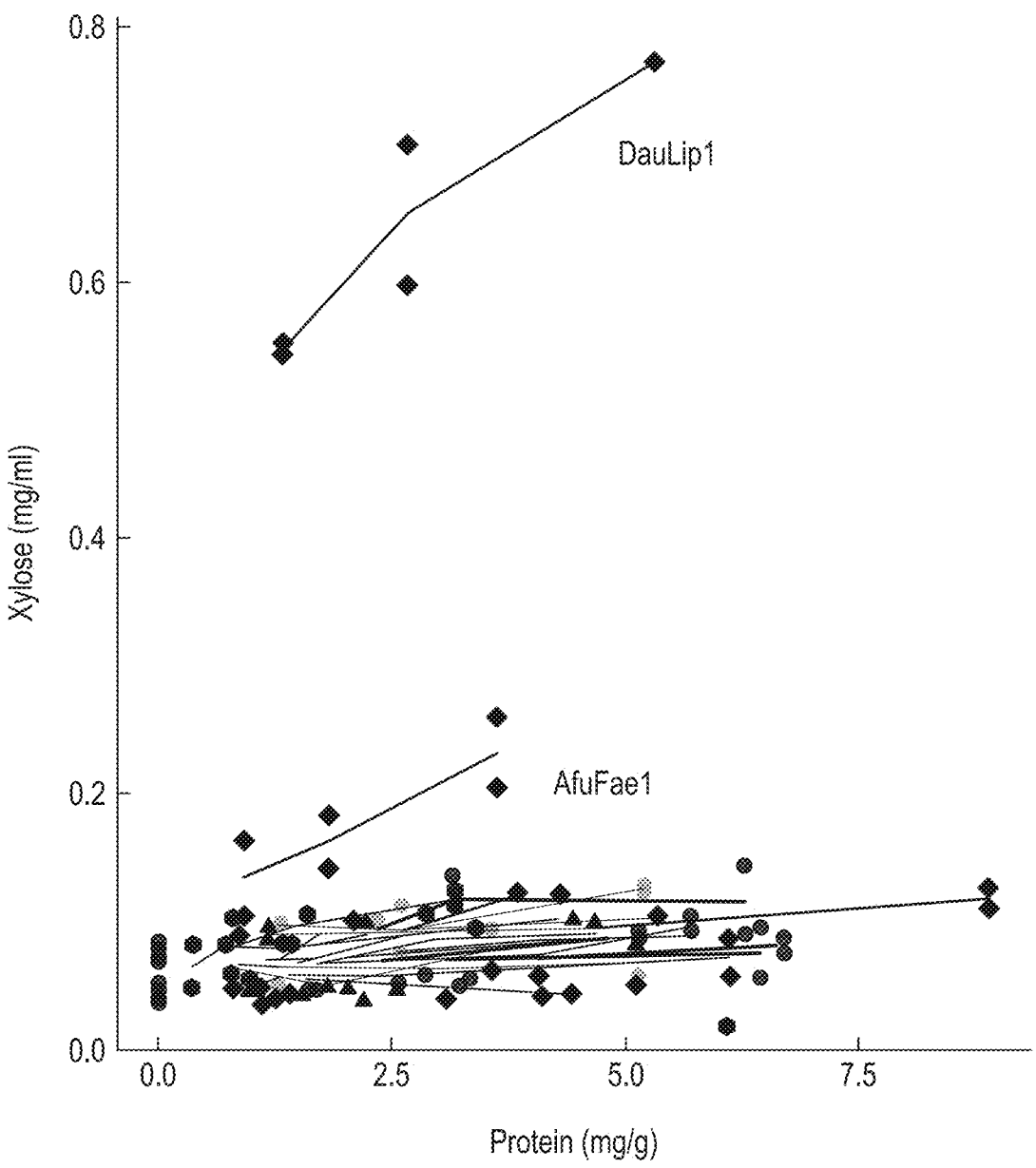
FIG. 2 shows xylooligomer release as the result of the addition of a group of 21 purified feruloyl esterases.
Figure 3:
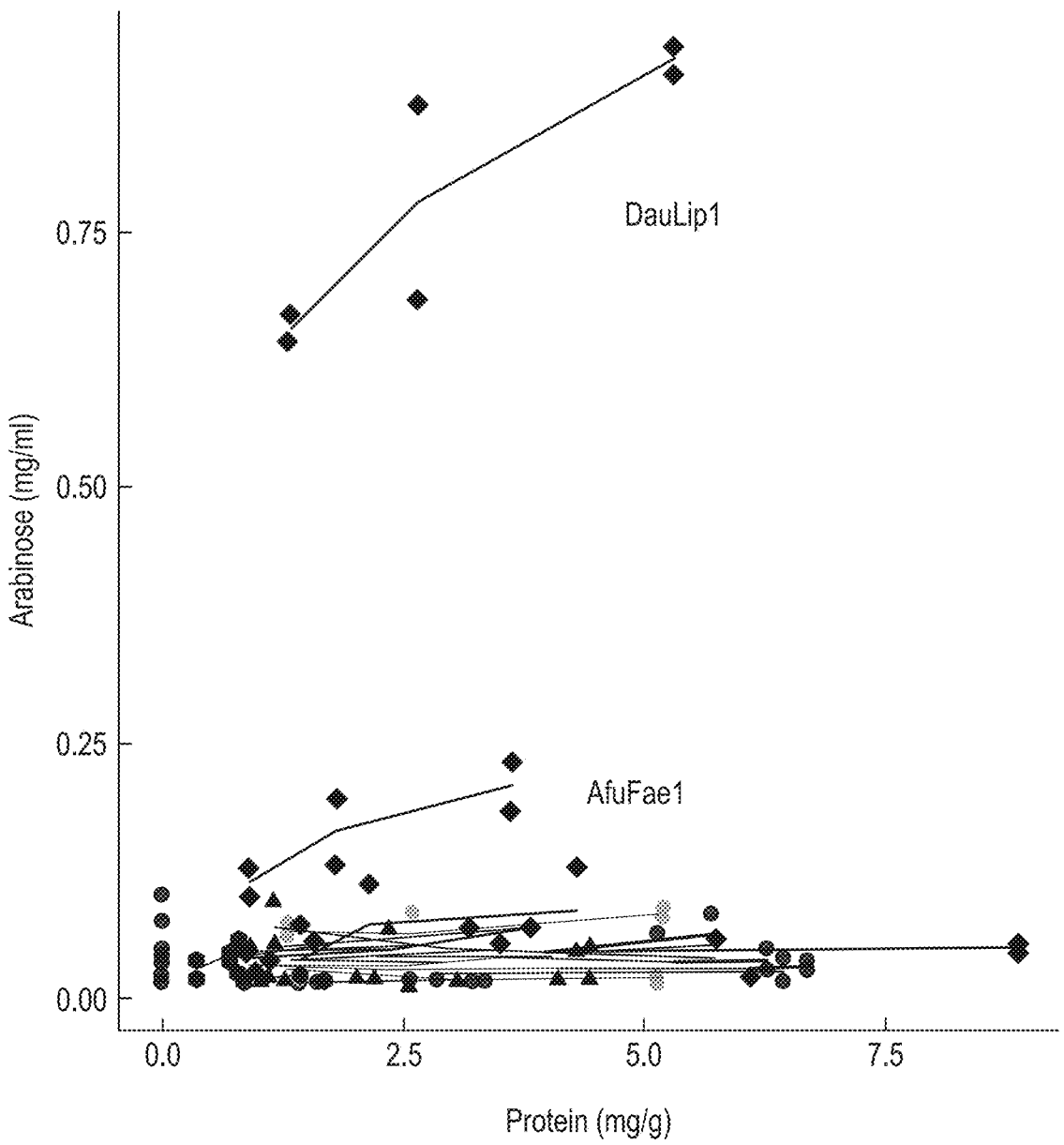
FIG. 3 shows arabinose containing xylooligomer release as the result of the addition of a group of 21 purified feruloyl esterases.
Figure 4:
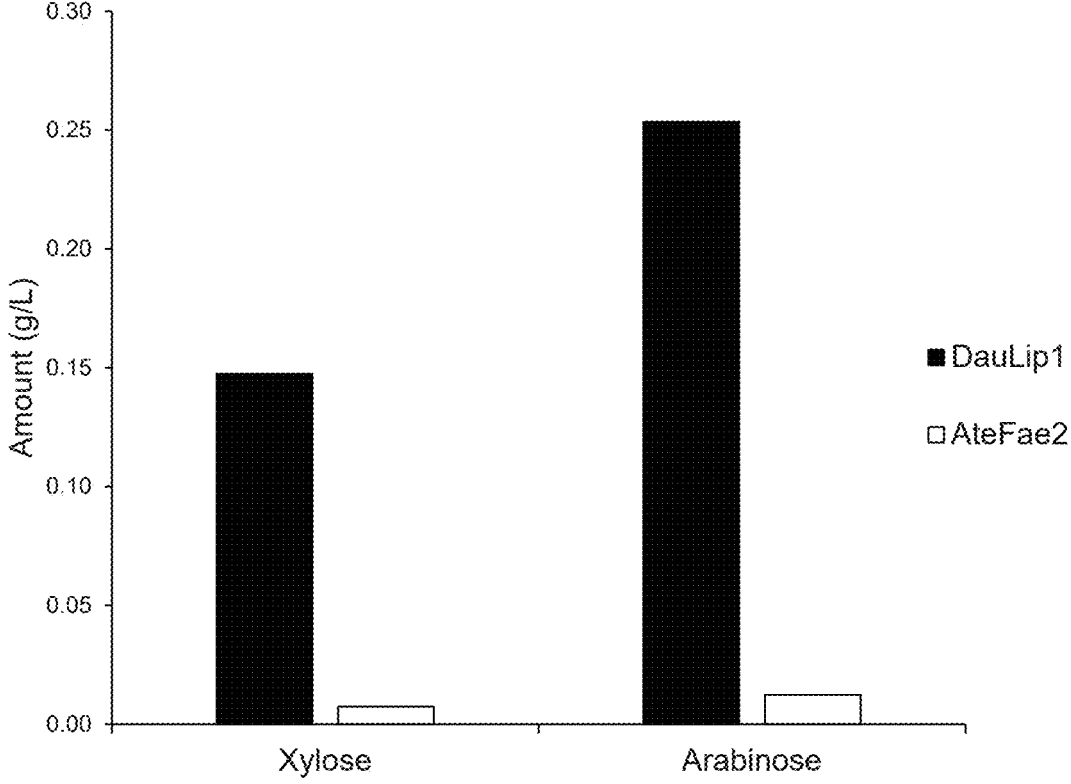
FIG. 4 shows arabinoxylan polymer liberation by DauLip1 evidenced by the sugar monomers released after acid hydrolysis. The feruloyl esterase AteFae2 is not able to liberate soluble arabinoxylan.

Feruloyl esterases and lipases. A group of 21 feruloyl esterases were cloned, expressed and purified. The expression method was the same as described in WO2018/164737. The enzyme doses were provided in FIGS. 2 and 3 as milligram protein per gram dry solid fiber. AfuFae1 (Example 5, FIGS. 2 and 3; Example 6, FIG. 5) corresponds to Accession No. XP_033410774 in the NCBI database with one amino acid substitution. AteFae2 (Example 6, FIG. 4) shares 91% sequence identity to accession No. XP_026625318 in the NCBI database. All micro-scale enzyme activity reactions (150 μL) of slurried, washed whole stillage solids were initiated by the addition of enzyme (5 μL, 10 μL and 20 μL). Reactions were incubated at 32° C. over night. After incubation, insoluble solids were removed by filtration. The soluble material was combined with sulfuric acid to a final concentration of 2%. The acidified supernatants were heated at 121° C. for 45 minutes. Autoclaved samples were cooled and diluted 10-fold in MilliQ water. Monomer glucose, xylose and arabinose were quantitated by HPLC (Rezex ROA-Fast Acid H+). DauLip1 produced significantly more xylo-oligomer than did the feruloyl esterase AfuFae1 (FIGS. 2 and 3). All other feruloyl esterases failed to produce a distinguishable increase of xylo-oligomer.

Example 6

Comparison of DauLip1 and Feruloyl Esterases

The substrate slurry was prepared by combining washed, milled whole stillage solids described earlier (3 g) and sodium acetate buffer (97 g of 20 mM, pH 5.0). A serial dilution of enzyme samples was prepared in MilliQ water. Enzyme sample (10 μL) was transferred into a new microtiter plate (Nunc, 267245) containing substrate slurry (140 μL). The final reaction concentration of both DauLip1 and AteFae2 or AfuFae1 was 10 ppm. The reaction was incubated at 32° C. with shaking (300 rpm) in incubation shaker (Infors HT, Multitron) for 24 hours. After incubation, the supernatant was collected by filtration using a filter plate

24

Figure 5:
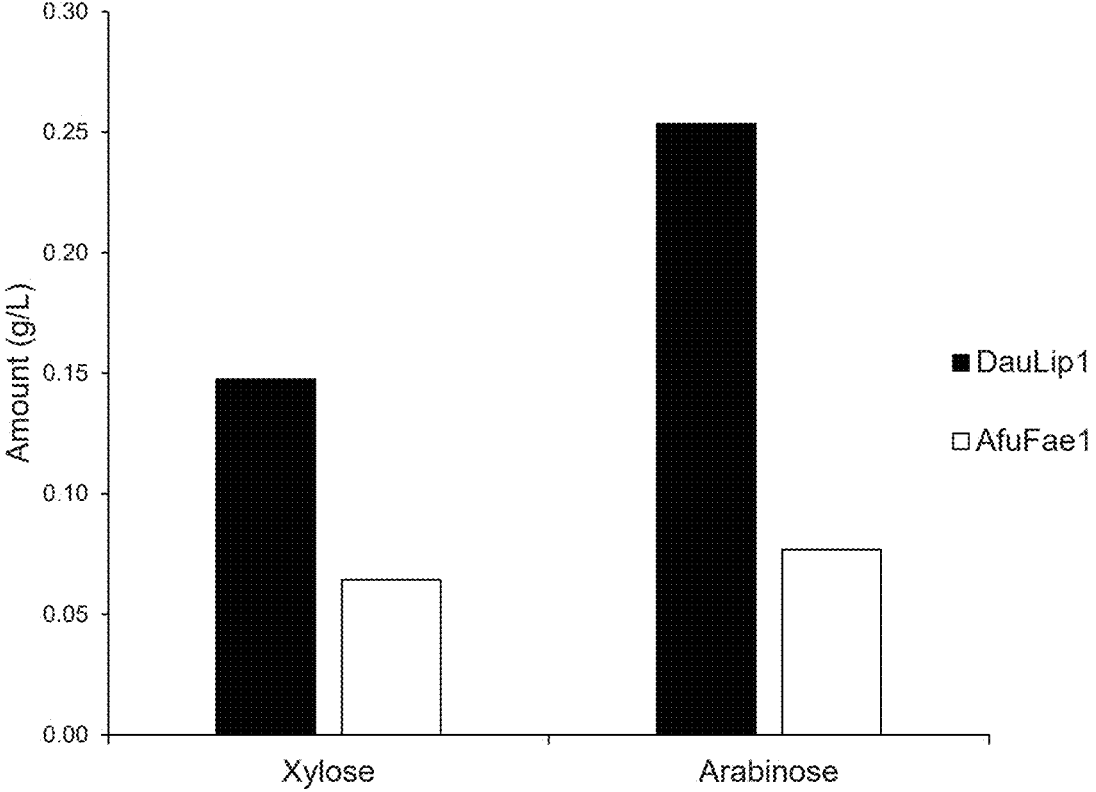
FIG. 5 shows arabinoxylan polymer liberation by DauLip1 evidenced by the sugar monomers released after acid hydrolysis. The feruloyl esterase AfuFae1 is not able to liberate soluble arabinoxylan.

(Corning 3505). Sulfuric acid solution (3 μL of 20% v/v) was added to a HS-PCR plate (Axygen) containing reaction supernatant or sugar recovery standard controls (27 μL). The samples and controls were autoclaved at 121° C. for 15 minutes. After cooling, the acid hydrolyzed samples and controls (10 μL) were added to MilliQ water (90 μL) and analyzed by HPLC using a Rezex ROA-Organic acid H+ column. DauLip1 liberates a larger amount of arabinoxylan from washed whole stillage solids than does the feruloyl esterase AteFae2 (FIG. 4) or AfuFae1 (FIG. 5).

Example 7

Comparison of DauLip1 Protein Sequence to Other Related Sequences

Related proteins were identified by a BLAST search (Altschul et al., Nucleic Acids Res, 25:3389-402, 1997) against the NCBI non-redundant protein database using the predicted mature amino acid sequence of DauLip1 (SEQ ID NO: 2) as query sequence and a subset of homologous proteins with greater than or equal to 66% identity to DauLip1 are shown on Table 4. Percent identity (PID) is defined as the number of identical residues divided by the number of aligned residues in the pairwise alignment.

TABLE 4

List of sequences with percent identity to DauLip1 protein identified from the NCBI non-redundant protein database

| NCBI Accession Number | putative enzyme/Organism name | % ID to WP_081971423. 1_DauLip1 |
|---|---|---|
| WP_081971423.1 DauLip1 | alpha/beta hydrolase [Dactylosporangium aurantiacum] | 100 |
| WP_155388305.1 | alpha/beta hydrolase [Catellatospora methionotrophica] | 78.9 |
| WP_166381138.1 | alpha/beta hydrolase [Catellatospora paridis] | 78.9 |
| WP_155373131.1 | alpha/beta hydrolase [Catellatospora vulcania] | 78.1 |
| WP_144126986.1 | alpha/beta hydrolase [Catellatospora sichuanensis] | 77.3 |
| WP_125490131.1 | alpha/beta hydrolase [Streptomyces sp. WAC 04229] | 67.8 |
| WP_084434874.1 | hypothetical protein [Kibdelosporangium aridum] | 67.3 |
| WP_116180173.1 | alpha/beta hydrolase [Kutzneria buriramensis] | 66.5 |
| WP_034215678.1 | alpha/beta hydrolase [Actinoplanes subtropicus] | 66.1 |

Figure 6:
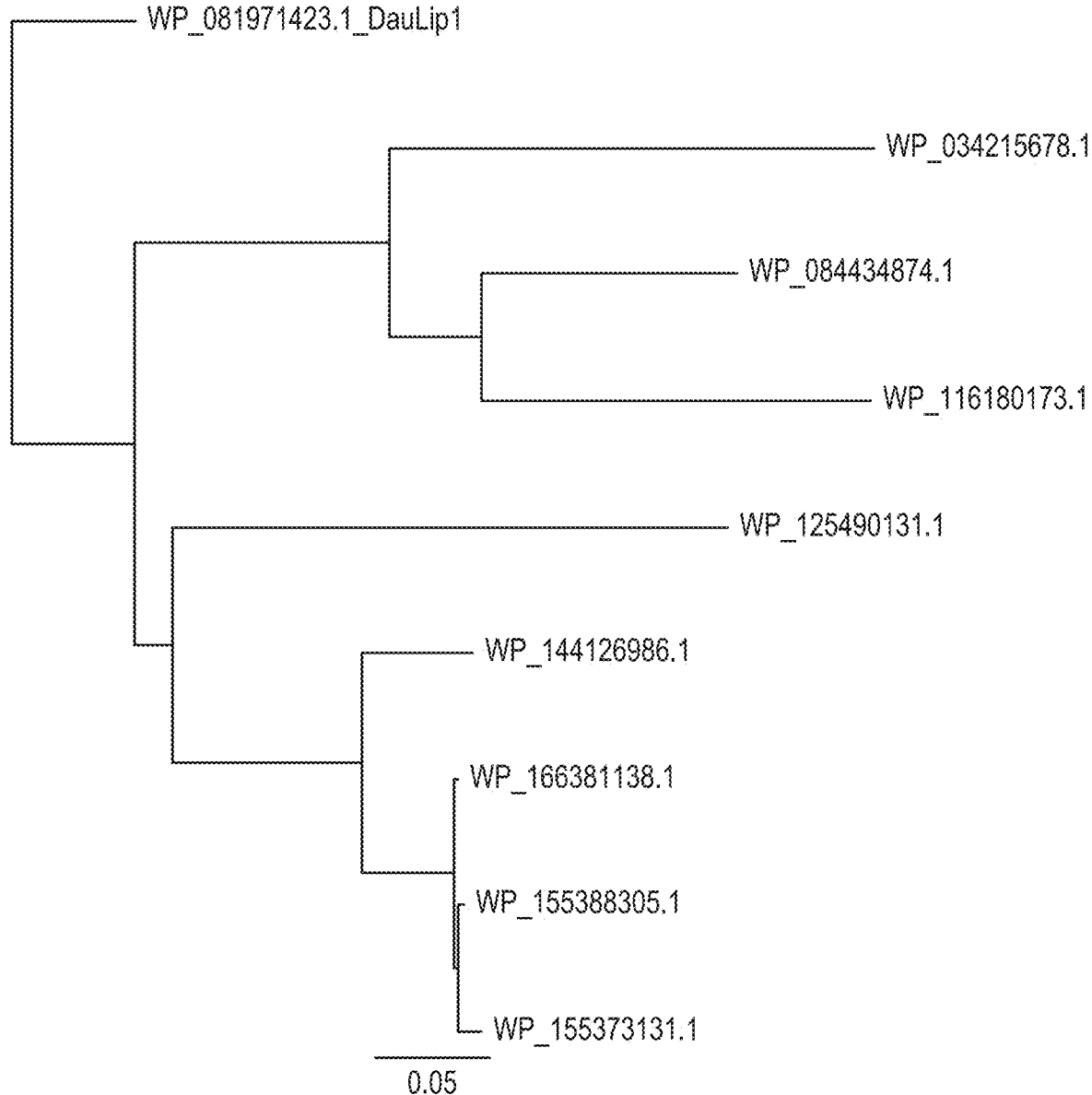
FIG. 6 shows a phylogenetic tree for amino acid sequences from the alignment by using the Geneious Tree builder program.

The sequences were aligned with default parameters using the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797). The N terminal portion of the sequences was trimmed to match with the starting amino acid sequence of the predicted mature DauLip1 sequence. A phylogenetic tree for amino acid sequences from the alignment was built using the Geneious Tree builder program and is displayed in FIG. 6.

What is claimed is:

1. A method for modifying an ester bond-containing polymer, comprising: contacting the ester bond-containing polymer with an effective amount of a polypeptide having polymer degradation or hydrolysis activity, wherein the polypeptide comprises an amino acid sequence having at least about 80% amino acid sequence identity to the amino acid sequence of SEQ ID NO:2, wherein the modification comprises hydrolysis of the ester bond, and wherein the ester bond-containing polymer is selected from the group consisting of polyethylene terephthalate (PET), polytrimethylene terephthalate (PTT) and arabinoxylan.

2. The method of claim 1, wherein the ester bond-containing polymer comprises pills on the surface of a fabric comprising the ester bond-containing polymer.

3. The method of claim 1, wherein the method further comprises contacting the ester bond-containing polymer with one or more cleaning agents selected from the group consisting of surfactants, builders, bleaching agents, dye transfer inhibiting agents, chelating agents, dispersants, polysaccharides, softening agents, suds suppressors, carriers, enzymes, enzyme stabilizing systems, polyacids, soil removal agents, anti-redeposition agents, hydrotropes, opacifiers, antioxidants, bactericides, dyes, perfumes, brighteners, and combinations thereof.

4. The method of claim 1, wherein the method further comprises contacting the ester bond-containing polymer with one or more enzymes selected from the group consisting of protease, hemicellulase, cellulase, peroxidase, esterase, xylanase, lipase, phospholipase, esterase, perhydrolase, cutinase, pectinase, pectate lyase, mannanase, keratinase, reductase, oxidase, phenoloxidase, lipoxygenase, ligninase, alpha-amylase, glucoamylase, pullulanase, beta-amylase, phytase, tannase, pentosanase, beta-glucanase, arabinosidase, laccase, transferrase, and combinations thereof.

5. A method of degrading a plastic product containing at least one ester bond-containing polymer comprising contacting the plastic product with an effective amount of a polypeptide comprising an amino acid sequence having at least 80% amino acid sequence identity to the amino acid sequence of SEQ ID NO: 2, and wherein the ester bond-containing polymer is selected from the group consisting of polyethylene terephthalate (PET), polytrimethylene terephthalate (PTT) and arabinoxylan.

* * * * *